(12) United States Patent
Heilek et al.

(10) Patent No.: US 7,637,965 B2
(45) Date of Patent: Dec. 29, 2009

(54) PROCESS FOR CONTROLLING A HYDRAULIC WASH COLUMN

(75) Inventors: Joerg Heilek, Bammental (DE); Klaus Joachim Mueller-Engel, Stutensee (DE); Ulrich Hammon, Mannheim (DE); Thomas Walter, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 613 days.

(21) Appl. No.: 11/400,406

(22) Filed: Apr. 10, 2006

(65) Prior Publication Data

US 2006/0237356 A1 Oct. 26, 2006

Related U.S. Application Data

(60) Provisional application No. 60/673,339, filed on Apr. 21, 2005.

(30) Foreign Application Priority Data

Apr. 21, 2005 (DE) .................. 10 2005 018 702

(51) Int. Cl.
*C30B 17/00* (2006.01)
(52) U.S. Cl. ...................... 23/301; 23/295 R
(58) Field of Classification Search ............... 23/295 R, 23/301
See application file for complete search history.

(56) References Cited

U.S. PATENT DOCUMENTS

| 3,267,686 | A | 8/1966 | Holley |
| 3,628,341 | A | 12/1971 | Klotz et al. |
| 5,831,124 | A | 11/1998 | Machhammer et al. |
| 6,780,206 | B2 * | 8/2004 | Nordhoff et al. ......... 23/295 R |
| 6,939,991 | B2 | 9/2005 | Thiel et al. |
| 7,323,016 | B2 * | 1/2008 | Heilek et al. ............. 23/295 R |
| 2003/0060661 | A1 | 3/2003 | Eck et al. |
| 2003/0175159 | A1 | 9/2003 | Heilek et al. |
| 2005/0006299 | A1 | 1/2005 | Heilek et al. |

FOREIGN PATENT DOCUMENTS

| DE | 196 06 877 A1 | 8/1997 |
| DE | 100 36 881 A1 | 2/2002 |
| DE | 102 35 847 A1 | 8/2003 |
| DE | 103 36 386 A1 | 3/2004 |
| EP | 0 097 405 A1 | 1/1984 |
| EP | 0 792 867 A2 | 9/1997 |
| EP | 1 015 411 | 7/2000 |
| WO | WO 99/14182 | 3/1999 |
| WO | WO 01/77056 A1 | 10/2001 |
| WO | WO 02/09839 A1 | 2/2002 |
| WO | WO 02/055469 A1 | 7/2002 |
| WO | WO 03/041832 A1 | 5/2003 |
| WO | WO 03/041833 A1 | 5/2003 |
| WO | WO 03/063997 A1 | 8/2003 |
| WO | WO 03/078378 A1 | 9/2003 |
| WO | WO 2004/035514 A1 | 4/2004 |

* cited by examiner

*Primary Examiner*—Edward M Johnson
(74) *Attorney, Agent, or Firm*—Oblon, Spivak, McClelland, Maier & Neustadt, L.L.P.

(57) ABSTRACT

A process for operating a hydraulic wash column, in which the position of the buildup front in the wash column is positioned by means of the flow rates of control liquor conducted into the wash column and/or by means of the flow rate of the suspension conducted into the wash column, and the flow rate determination is with the aid of the pressure difference which exists in the column between points in the suspension zone disposed upstream of the buildup front and points in the zone projecting from the buildup front up to the end of the crystal bed.

8 Claims, 3 Drawing Sheets

PROCESS FOR CONTROLLING A HYDRAULIC WASH COLUMN

BACKGROUND OF THE INVENTION

1. Field of the Invention

The present invention relates to a process for controlling a hydraulic wash column (cf. FIG. 1, to which the numerical addresses which follow and the numerical addresses in the claims relate) which has a cylindrical shell (1) which delimits the column and within which one or more filter tubes (2) extend through the column parallel to the cylinder axis and have, in the vicinity of the second end of the column, at least one filter (3) in the filter tube wall which forms the sole direct connection between the filter tube interior under the pressure P1 and the interior of the column, in which at least one stream of a suspension (4) which comprises crystals of a substance to be purified (to be removed in maximum purity) suspended in a mother liquor is fed continuously into the first end of the column (5) with a pressure P2 (for example by means of a pump (6)) which is greater than P1, mother liquor (7) is conducted through the filters into the filter tube interior and out of the column via the filter tubes, if appropriate, control liquor (9) is fed into the wash column at the first end of the column and/or between this end and the start of the filter, the mother liquor and, if appropriate, control liquor flow in the column form a crystal bed (10) of the substance to be purified, said crystal bed having a buildup front (11) which faces the first end of the column and at which crystals of the introduced suspension add continuously to the crystal bed, the crystal bed, by virtue of the force resulting from the hydraulic flow pressure drop of the mother liquor and, if appropriate, control liquor flow in the column, is transported (13) past the filters into the wash zone disposed between the filters and the second end of the wash column (12), crystals are removed (14) continuously at the opposite end of the crystal bed to the buildup front, the removed crystals are melted (15) and a portion of the melt is passed (16) through the crystal bed as a wash liquid stream coming from the second end of the column against the transport direction of the crystals and the position of the buildup front is controlled with the aid of the flow rate of control liquor conducted into the wash column and/or with the aid of the flow rate of the suspension (4) conducted into the wash column.

2. Description of the Background

In particular, the present invention relates to the control of a hydraulic wash column which is operated for the purifying removal of acrylic acid crystals from their suspension in contaminated acrylic acid, as is described in the documents WO 01/77056, WO 04/35514, WO 03/41833, WO 02/9839, WO 03/41832, DE
A 100 36 881, WO 02/55469 and WO 03/78378. The numerical addresses in this document always relate to the figures appended to this document.

In this document, the terms cylindrical and tubular should be understood so as to comprise all geometric shapes (bodies) whose cross section is circular or circle-like (for example elliptical or polygonal (for example regular tetragon, hexagon or octagon).

In this document, the term mother liquor should be understood so as to comprise in particular melts composed of the substance to be purified and impurities and/or also solutions of the substance to be purified and solvents or solvent mixtures and also impurities. Equally, the term "melt of removed crystals as a wash liquid stream" should preferably comprise melts of removed crystals but also saturated solutions of removed crystals in solvents or solvent mixtures. Correspondingly, "melting of removed crystals" also comprises "saturating dissolution of removed crystals in solvents or solvent mixtures". Acrylic acid, either itself or in the form of its salts or its esters, is of significance especially for the preparation of polymers for a wide variety of fields of use (for example adhesives, superabsorbants, binders).

The process according to the preamble of this document is known (cf., for example, EP-A 097 405, WO 03/041832, DE-A 100 36 881, WO 02/09839, WO 03/041833, WO 01/77056 and WO 03/063997).

The process generally follows a suspension crystallization which forms a very effective and inexpensive process for achieving a high purity of a desired chemical compound (of a chemical substance).

This is because, in the synthesis of a chemical compound, the desired substance typically does not occur as a pure product, but rather as a portion of a compound mixture which, in addition to the desired substance, comprises impurities such as unconverted starting compounds, solvents, by-products or undesired isomers.

When the desired substance is a crystallizable compound (for example acrylic acid) which is present in a liquid compound mixture after the synthesis process or can be converted into one (cf., for example, EP-A 1 015 411, DE-A 196 06 877, DE-A 103 36 386, EP-A 792 867, DE-A 102 35 847, WO 03/078378, WO 02/055469 in the case of acrylic acid or methacrylic acid), suspension crystallization (especially from the melt) is recommended as a purification process for the desired substance, which forms a very effective and inexpensive process for achieving a high purity of a desired chemical compound.

This utilizes the fact that impurities are substantially expelled from the crystal lattice in the course of growth of the crystals in a liquid and remain in the mother liquor. Suspension crystallization has the advantage over layer crystallization that it can be carried out in a continuous process. Moreover, the purity of the crystals is very high owing to their comparatively slow growth rate. In spite of the relatively slow growth rate, it is possible with suspension crystallization to achieve a high product throughput, since the crystallization is associated with a large total surface area available for growth owing to the large number of simultaneously growing crystals.

Even in a one-stage crystallization process, highly pure crystals of the desired compound are thus obtained. In principle, the suspension crystallization can be effected either from a solution or from a melt.

A decisive step which has a crucial influence on the purity of the crystallized target product is the removal of the highly pure crystals from their mother liquor, which comprises the impurities in enriched form and the uncrystallized fractions of the target product, by a solid/liquid separation process.

For the aforementioned separation task, it has been found to be useful to use wash columns. They comprise a generally cylindrical wall (shell) which delimits a process chamber.

Frequently disposed upstream of the process chamber is a distributor chamber into which the crystal suspension to be separated in the wash column is fed. On its path from the distributor chamber into the process chamber, the crystal suspension is distributed substantially uniformly over the cross section of the process chamber. In the process chamber, a denser crystal bed is obtained, especially by mother liquor removal, and conducted through the process chamber (in columns with forced transport of the crystal bed, this may either be from the top downward or from the bottom upward). The cross section of the process chamber is normally constant over its length. The wash liquid passed through the crystal bed in countercurrent is a melt of crystals which have been removed beforehand in the column (or a saturated solution thereof in solvents or solvent mixtures).

For the formation of a dense (compact) crystal bed in the wash column, different methods are employed in practice. In wash columns which operate under gravity, the crystal suspension is introduced into the column from the top and the crystal bed is formed in a sedimentation process with sole conveying action by gravity. Separation processes in such wash columns are not provided by the process according to the invention.

Wash columns with forced transport (or conveying) of the crystal bed differ from such gravimetric wash columns in that, in the conveying direction (or transport direction) of the crystal bed, at least one conveying force other than gravity acts.

In principle, wash columns with forced transport of the crystal bed are divided into pressure columns (also known as hydraulic wash columns or hydraulic columns) and into mechanical columns.

Mechanical wash columns comprise a mechanical forced conveying unit for the crystals. In the simplest case, this may be a semipermeable plunger which is permeable to the mother liquor but impermeable to the crystals in the suspension supplied (cf. FIG. 3 of WO 03/041832) and which shifts to generate the pressure for the compaction and conveying of the crystal bed. In a mechanical wash column, a crystal bed can also be compacted and conveyed by removal of the mother liquor through filters and mechanical transport of the crystals from the filter to the crystal bed by a rotating conveying element (for example screws, stirrers, helices or spirals) (cf. FIG. 4 of WO 03/041832). The filters may also be integrated into the rotating conveying elements. Separating processes in mechanical wash columns are not provided by the process according to the invention.

Figure 1:
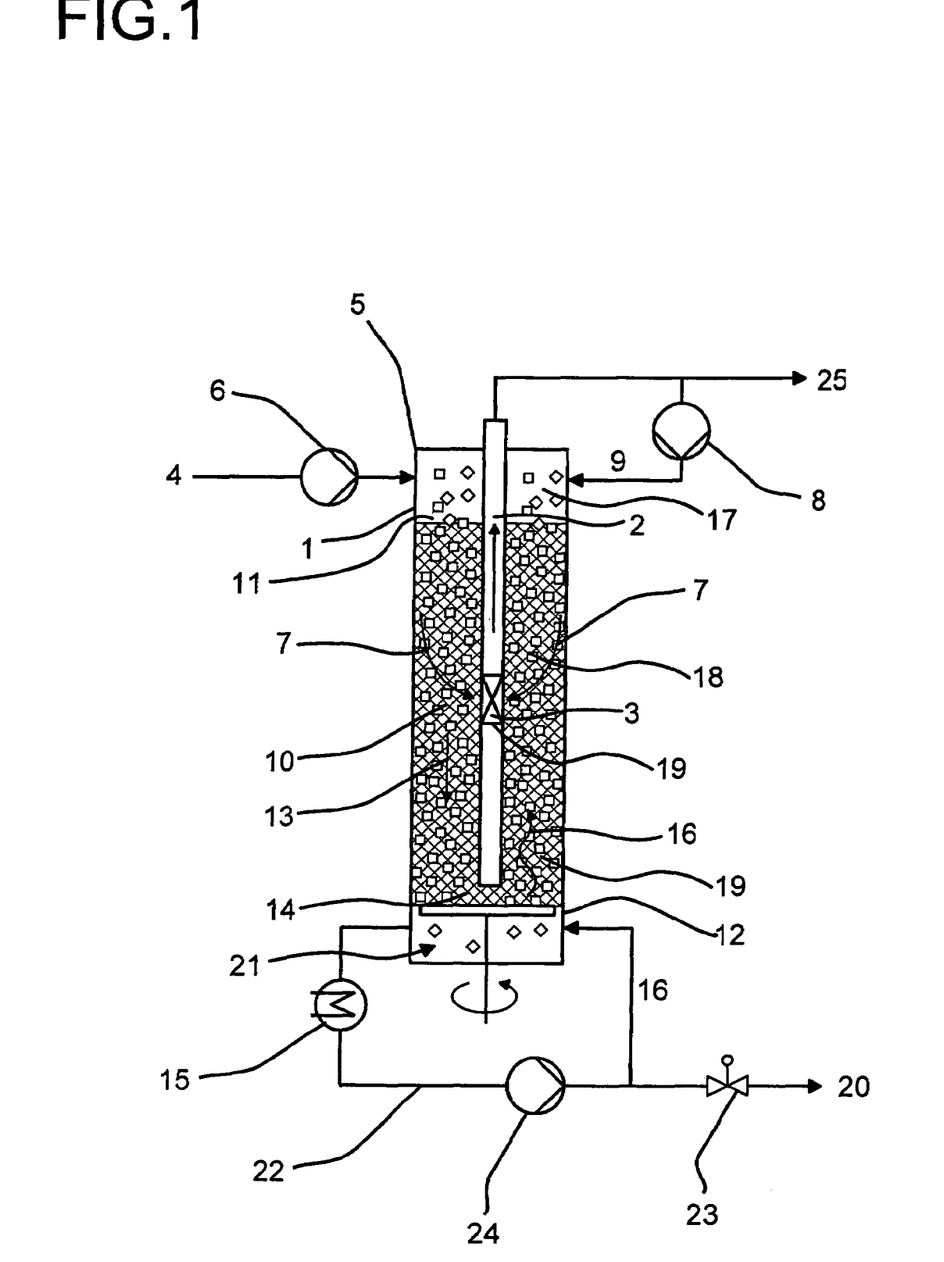
FIG. 1 is a hydraulic wash column according to the present invention.

In the hydraulic wash columns relevant to the process according to the invention, the crystal suspension is conveyed at one end of the wash column into the cylindrical wash column under pressure (for example by pumps (6) according to FIG. 1 or by hydrostatic head). In parallel to the cylinder axis, at least one filter tube ((2) in FIG. 1) extends through the column and has, pointing away from the crystal suspension feed, at least one filter ((3) in FIG. 1) which forms the sole direct connection between the filter tube interior under a pressure P1 and the interior of the column.

Typically, the filter tubes project into the wash zone, but are no longer hollow in this region of the wash column (cf., for example, WO 01/77056, WO 03/41833 and WO 03/41832). This part of the filter tubes is also referred to as the filter tube displacer.

The liquid flow imposed by the feed column pressure P2 >P1 generates compaction of the crystals to a crystal bed and the conveying thereof. The mother liquor flows through the filters out of the wash column (beyond the filters, the pressure may be standard pressure, reduced pressure or superatmospheric pressure). The crystal bed has a so-called buildup front ((11) in FIG. 1) at which crystals of the introduced crystal suspension add on continuously. The buildup front thus denotes the transition from the suspension to the crystal bed and is indicated by a relatively abrupt rise in the crystal content in the suspension. It separates the suspension zone ((17) in FIG. 1) from the crystal bed. In many cases, the buildup front is also referred to as the filtration front. At the opposite end of the crystal bed to the buildup front, washed crystals are continuously removed ((14) in FIG. 1). This may be effected, for example, by means of a kind of rotor blade or with the aid of scrapers, which remove crystals continuously from the crystal bed. The continuous crystal removal may also be effected as described in WO 03/063997. There, suitable impulse on the wash melt brings about continuous disintegration of crystals from the crystal bed. The continuous addition of crystals to the buildup front on the one hand and the continuous removal of washed crystals at the opposite end of the crystal bed to the buildup front on the other hand define the transport direction of the crystal bed (it may either point from the top downward or from the bottom upward). The crystals removed from the crystal bed, preferably after they have been resuspended in pure melt (or in solvents or solvent mixtures) are melted by heat transfer (or dissolved, preferably in a saturating manner). A portion of the melt (of the pure melt) is removed as pure product stream ((20) in FIG. 1) and another portion of the pure melt is recycled (forced back) into the process chamber as wash liquid against the transport direction of the crystal bed at its end facing away from the buildup front. Typically, the wash liquid is at the melting point. Preference is given to effecting the resuspension in a separate chamber (the suspension chamber) adjoining the end of the crystal bed (typically not included in the wash column), into which, for example, the rotor blade introduces the removed crystals ((21) in FIG. 1). This suspension is then appropriately conducted in a melt circuit ((22) in FIG. 1) through a heat carrier ((15) in FIG. 1), by means of which the heat required to melt the crystals is introduced by an indirect route. Frequently from 70 to 80% by weight, in favorable cases (for example in the event of marked recrystallization in the wash zone) even from >80 to 100% by weight, of the molten crystals are removed as pure product ((20) in FIG. 1) from the melt circuit. The amount of pure product withdrawn is appropriately adjusted by means of a product regulating valve ((23) in FIG. 1). The conveying in the melt circuit is effected advantageously with a conveying pump ((24) in FIG. 1). The circulation rate in the melt circuit is advantageously from 2 to 30 m$^3$/h, usually from 5 to 20 m$^3$/h per m$^3$ of removed purified crystals (calculated in molten form). In other words, the resuspension has a low crystal content favorable in performance terms, which promotes the conveying thereof.

How much pure melt penetrates from the melt circuit as wash melt into the wash column is appropriately controlled via the pressure in the melt circuit (suspension chamber) (this is determined indirectly by means of the adjustment of the product regulation valve). In general, this is a portion of the removed amount of crystals.

However, the melting of the removed crystals can also be undertaken directly within the wash column (for example by means of appropriately installed apparatus for heating at the end of the process chamber facing away from the buildup front). In this case, only a portion of the melt generated is withdrawn from the column. The other portion ascends as wash melt within the hydraulic wash column.

As a result of the conveying of the pure melt counter to the conveying direction of the crystal bed, the crystal bed, which has been impregnated with the mother liquor in particular, is virtually forced into the pure melt (and vice versa), and the mother liquor in the crystal bed is essentially simply forced back by the pure melt ("to form a substantially stable phase boundary between pure melt and mother liquor").

In the steady state (operation), the result of this process at a defined height of the crystal bed (disposed between filter and crystal removal) is a wash front ("phase boundary") which is defined as that point in the crystal bed where the highest temperature and concentration gradients occur (within the wash front, the phase transition is effectively from pure melt to mother liquor (or mixture of mother liquor and control liquor); in the wash front, the temperature virtually jumps from the lower mother liquor temperature to the higher pure melt temperature; above and below the wash front, the temperatures are substantially constant). Since pure melt and mother liquor (as already stated), expressed in coarse terms, collide with one another in the wash front, there is also a concentration jump of the undesired impurities at the height of the wash front from mother liquor concentration to pure melt concentration. The region from the wash front to the buildup front is referred to as the mother liquor zone and the region from the wash front to the end of the crystal bed facing away from the wash front is referred to as pure melt zone.

Since the crystallization temperature in the contaminated suspension is below the pure product melting point, there is also a temperature equalization of the cold crystals with the wash melt in the region of the wash front, in which the wash melt recrystallizes partly or fully. This recovers at least a portion of the wash melt. The other portion leaves the wash column together with the removed mother liquor through the filters and can, for example, be recycled into the recovery of the liquid compound mixture to be purified, or further purified ((25) in FIG. 1) and/or, if appropriate, used at least partly as control liquor which is yet to be described below ((9) in FIG. 1).

The further the crystallization temperature in the mother liquor is below the melt temperature of the pure product (or the saturation temperature of the wash solution), the more marked the described recrystallization of the wash melt (typical temperature differences are from 5 to 15 K). When recrystallization is quantitative, 100% of the molten crystals can be removed as pure product from the already described melt circuit ((22) in FIG. 1).

The cross section of the process chamber of a hydraulic wash column may be circular, oval or angular (for example regular-polygonal).

To achieve an adequate purifying action in the wash zone (the portion of the crystal bed which starts at the crystal removal and extends up to the start of the filter), the wash front has to be positioned at a certain minimum height above the crystal removal. In a similar manner, the buildup front also has to be well positioned in order to ensure effective operation of a hydraulic wash column.

Since the crystal bed is transported by the force resulting from the hydraulic flow pressure drop of the mother liquor (or mother liquor and control liquor) past the filters into the wash zone beyond the filters, it is energetically unfavorable for the operation of a hydraulic wash column when the concentration zone (the region of the crystal bed from the buildup front up to the start of the wash zone) is too elongated. With increasing length of the concentration zone, friction and the associated flow pressure drop increase. Conversely, an insufficient length of the concentration zone is disadvantageous in that it may be insufficient to form an adequately compacted crystal bed. Moreover, an excessively low flow pressure drop is incapable of fully satisfactorily transporting the crystal bed.

To ensure stable operation of a hydraulic wash column, i.e. to ensure a defined space-time yield at constantly good purifying action, constant compensation of external disrupting factors which impact upon the position of wash front and buildup front is required. Such disrupting factors may, for example, be variations in the flow rate of the suspension, changes in the crystal content in the suspension, variations in the crystal size distribution or else variations in the product mixture from the synthesis process fed to the crystallizer.

The position of the wash front is typically controlled by the setting of the amount of wash melt. This can be done, for example, as described in the documents DE-A 100 36 881 and WO 02/09839.

Since the position of the buildup front and filtration front is influenced by the hydraulic conditions (they determine the advance rate of the crystal bed) in the wash column, one possibility according to the teachings of DE-A 100 36 881 and WO 02/09839 is to influence the hydraulic pressure drop and hence to influence the advancing force in the wash column by pumping back a portion of the mother liquor removed by means of the filters (and if appropriate wash melt and also if appropriate control liquor) as control liquor ((9) in FIG. 1) into the wash column at the opposite end to the crystal removal and/or between this end and the start of the filter (if appropriate, control liquor is pumped in simultaneously at several points). The flow rate of control liquor to be recycled is appropriately adjusted by means of a corresponding control stream pump ((8) in FIG. 1), for example by changing the rotational speed and/or an additional regulating valve. However, useful control liquors are in principle also melts and/or solutions (which are preferably saturated with the substance to be purified) which comprise the substance to be purified and are different from mother liquor or identical to mother liquor, which can be drawn from external sources (i.e. not drawn from the wash column itself) (for example from the crystallizer and/or other process stages in the course of the preparation of the substance to be purified). It will be appreciated that the control liquors used may also be mixtures of control liquor types addressed above and below. Instead of by means of a pump, the control liquor may also be forced into the wash column by hydrostatic head. It is of course also possible to combine both feed variants. For example, the control liquor used may also be mother liquor which is withdrawn directly from the crystallizer used to prepare the suspension stream ((4) in FIG. 1) or the suspension disposed therein. The control liquor preferably does not have a higher purity than the mother liquor in order to substantially prevent recrystallization in the concentration zone. In other words, the starting melt used for the suspension crystallization itself is also useful as control liquor. Further useful control liquors are liquids in which the substance to be purified is firstly sparingly soluble to entirely insoluble and which secondly have a solidification point which is below the temperature of the crystal suspension fed to the wash column. When, for example, in continuous operation, the crystal bed ascends in the hydraulic wash column according to FIG. 1 (the buildup front shifts upward), the flow rate of the control liquor (and with it the hydraulic flow pressure drop of the mother liquor and control stream liquor in the wash column) increases, and, in the event of a descending crystal bed, it is reduced. The change in the flow rate of the control liquor can be carried out according to a defined characteristic, for example as a linear change in amount flow rate with time. Alternatively or additionally, the flow rate of the suspension (4) itself can correspondingly be increased or reduced to control the position of the buildup front.

When control liquor is forced into the wash column between the opposite end of the wash column to the crystal removal and the start of the filter at several points (at several heights) (this normally has to be done with different pressures; appropriately, these can be established by means of valves and correspond to the pressure existing at the particular feed point in the wash column or are slightly above them) (at the same time, the control liquors forced into the wash column may also have different chemical compositions; they are preferably chemically identical), an increase or decrease in the (total) control amount stream can be performed in such a way that the contribution of each individual control liquor stream is increased or reduced. Advantageously, the aforementioned increase or decrease is effected in such a way that the ratio of the control stream volumes fed per unit time at the different points relative to one another remains constant. It will be appreciated that the liquor control streams may also comprise "blank streams". These are control liquor streams whose magnitude is kept stable irrespective of the behavior of the buildup front. They essentially form a base contribution to the control. Preferably only one control stream will be used, and will preferably be forced (pumped) (with the pressure P2) into the wash column (into the suspension zone) at the opposite end to the crystal removal. Advantageously, this control stream consists exclusively of liquor conducted out of the wash column through the filter tubes ((9) in FIG. 1) and is appropriately conducted (pumped) into the wash column by means of the control pump S ((8) in FIG. 1).

In principle, however, the control liquor stream can also be fed into the wash column by feeding the control liquor stream, for example upstream and/or downstream of the pump (6), into the suspension stream (4) to be fed to the wash column.

To monitor the position of the buildup front and filtration front, both WO 02/09839 and DE-A 100 36 881 recommend optical detection of the position. However, a disadvantage of optical detection of the position is that, at least at the point of detection, the cylindrical shell of the wash column has to consist of a transparent material (for example glass). However, the shell of the process chamber of a hydraulic wash column is preferably (cf., for example, WO 03/041832) manufactured from metal. Although it is possible in principle to install transparent windows in a metal wall, pressure-tight (as is required in the case of a hydraulic wash column) manufacture thereof is not simple in engineering terms and their use, especially in the case of hazardous substances, is not uncontroversial in safety terms. Furthermore, point monitoring through windows with restricted view is not fully satisfactory. Instead, what is desirable is a monitoring variant which captures (views) the entire length of the concentration zone. In addition, optical sensors are comparatively expensive.

It was an object of the present invention to provide an improved process for regulating the position of the buildup front within a hydraulic wash column, in which the flow rate of control liquor and/or suspension to be conducted into the hydraulic wash column at the particular time is determined by using a more advantageous parameter than in the prior art.

SUMMARY OF THE INVENTION

Accordingly, a process has been found for controlling a hydraulic wash column which has a cylindrical shell (1) which delimits the column and within which one or more filter tubes (2) extend through the column parallel to the cylinder axis and have, in the vicinity of the second end of the column, at least one filter (3) in the filter tube wall which forms the sole direct connection between the filter tube interior under the pressure P1 and the interior of the column, in which at least one stream of a suspension (4) which comprises crystals of a substance to be purified suspended in a mother liquor is fed continuously into the first end of the column (5) with a pressure P2 (for example by means of a pump (6)) which is greater than P1, mother liquor (7) is conducted through the filters into the filter tube interior and out of the column via the filter tubes, if appropriate, control liquor (9) is fed into the wash column at the first end of the column and/or between this end and the start of the filter, the mother liquor and, if appropriate, control liquor flow in the column form a crystal bed (10) of the substance to be purified, said crystal bed having a buildup front (11) which faces the first end of the column and at which crystals of the introduced suspension add continuously to the crystal bed, the crystal bed, by virtue of the force resulting from the hydraulic flow pressure drop of the mother liquor and, if appropriate, control liquor flow in the column, is transported (13) past the filters into the wash zone disposed between the filters and the second end of the wash column (12), crystals are removed (14) continuously at the opposite end of the crystal bed to the buildup front, the removed crystals are melted (15) and a portion of the melt is passed (16) through the crystal bed as a wash liquid stream coming from the second end of the column against the transport direction of the crystals and the position of the buildup front is controlled with the aid of the flow rate of control liquor conducted into the wash column and/or with the aid of the flow rate of the suspension (4) conducted into the wash column, wherein the flow rates of the control liquor and/or suspension (4) conducted into the wash column are determined (regulated) by using (employing) at least one pressure difference $\Delta P_{SK}$ which exists in the column between at least one point in the suspension zone disposed in front of the buildup front (17) and at least one point in the zone projecting from the buildup front up to the end of the crystal bed (preferably in the concentration zone (18), projecting up to the start of the wash zone (19), of the crystal bed).

DETAILED DESCRIPTION OF THE INVENTION

Preferably in accordance with the invention, the pressure differences $\Delta P_{SK}$ are employed to determine the flow rate of control liquor and/or suspension (4) conducted into the wash column in their form $\Delta P_{SKB}$ adjusted by the hydrostatic pressure difference.

Figure 2:
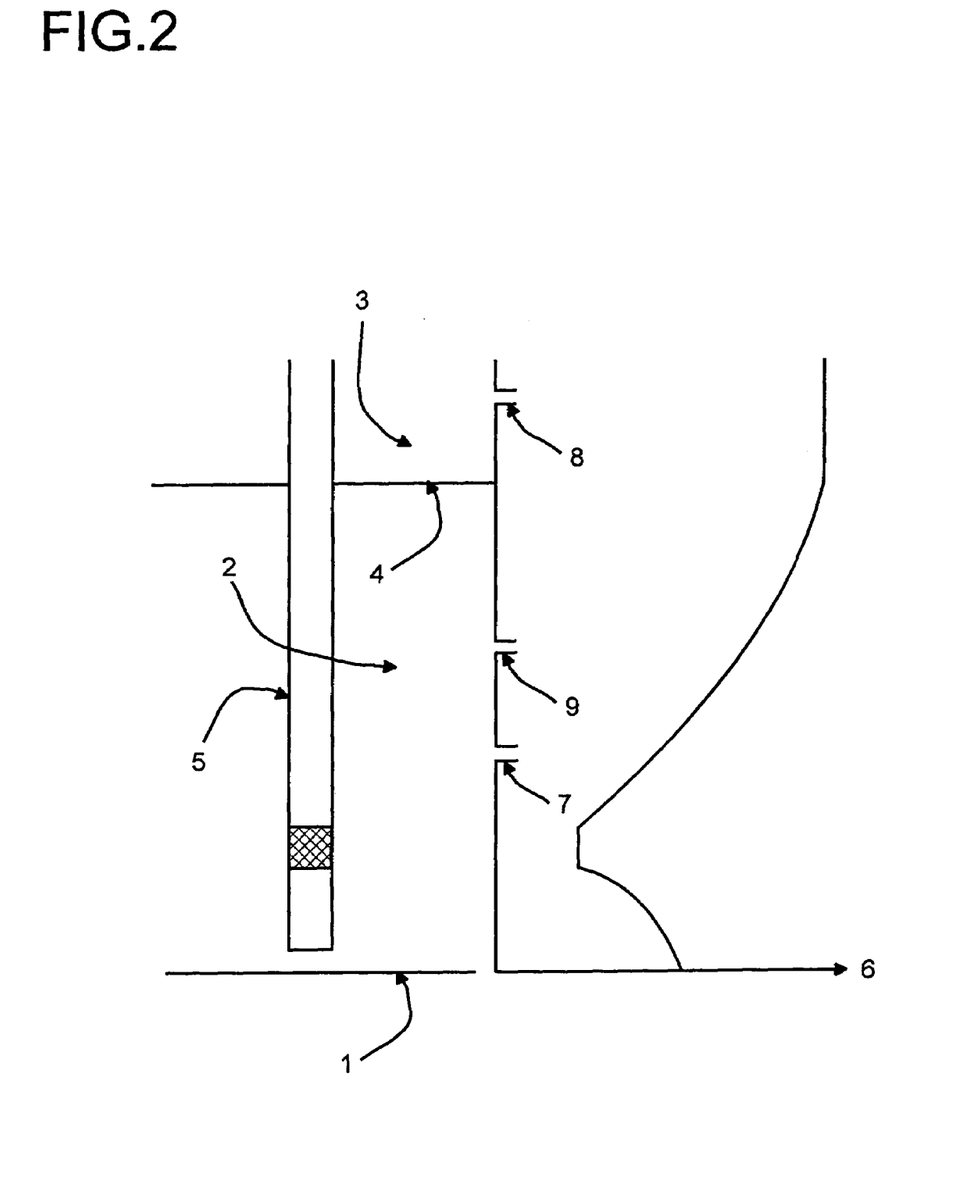
FIG. 2 is a hydraulic wash column showing drill holes for experimentally deriving $\Delta P_{SK}$.

The bases for the process according to the invention are the pressure conditions which have been adjusted by the hydrostatic pressure and are shown schematically in FIG. 2 for a hydraulic wash column. In this figure, the numerical addresses are defined as follows:

1=means (for example rotor blade) for continuously removing crystals from the crystal bed
2=crystal bed
3=suspension zone 4=buildup front
5=filter tube
6=pressure, adjusted by the hydrostatic pressure, within the hydraulic wash column as a function of its length The phrase "pressure adjusted by the hydrostatic pressure" means the pressure existing at a certain point in the hydraulic wash column minus the "hydrostatic" pressure existing at this point. For linguistic simplification, this pressure will be referred to in this document as "adjusted pressure" P. The term hydrostatic pressure means the pressure exerted by the weight of the column disposed above this point.

Within the suspension zone, the adjusted pressure is substantially constant and is at the driving pressure level P2. Subsequently, it falls progressively beyond the buildup front within the crystal bed (within the concentration zone) down to filter height.

At the height of the crystal removal, the adjusted pressure is at the wash pressure level. This is the pressure with which the wash melt is recycled into the wash column. This pressure equally decreases within the wash zone (frequently approximately linearly). Driving pressure and wash pressure are in a fixed ratio relative to one another depending on the friction.

When the difference is now determined between the adjusted pressure of a point within the suspension zone and the adjusted pressure of a point within the zone projecting from the buildup front up to the end of the crystal bed (preferably within the concentration zone), this pressure difference $\Delta P_{SKB}$ is a measure of the immediate operating state of the wash column and can be employed in an advantageous manner to determine the flow rates of control liquor and/or suspension to be conducted into the wash column.

In the case of large $\Delta P_{SKB}$ values, as frequently occur in practice on the grounds of a maximum space-time yield and resulting maximum column throughputs and driving pressures, the fraction resulting from the hydrostatic pressure difference in the unadjusted $\Delta P_{SK}$ value accompanying a $\Delta P_{SKB}$ value is small and negligible within the required and desired regulating precision.

In these cases, it is also possible to employ for the process according to the invention the direct $\Delta P_{SK}$ values in their form unadjusted by the hydrostatic pressure difference (by the hydrostatic differential pressure) to determine the flow rates of the control liquor and/or suspension (4) to be conducted into the wash column.

However, preference is given in accordance with the invention, especially in the context of regulation of the flow rates of control liquor and/or suspension (4) to be fed to the wash column with increased precision, to employing $\Delta P_{SK}$ values adjusted by the hydrostatic differential pressure, i.e. $\Delta P_{SKB}$ values, for this determination.

In the remarks which follow, $\Delta P_{SK}$ therefore represents "$\Delta P_{SK}$" and "$\Delta P_{SKB}$" unless stated otherwise. In other words, anything which is stated below to apply to $\Delta P_{SK}$ also applies to the corresponding $\Delta P_{SKB}$.

Preferably in accordance with the invention, all reference points which lie within the zone projecting from the buildup front up to the end of the crystal bed and are employed to determine a $\Delta P_{SK}$ are disposed in the region between the crystal removal and the next feed point of a control stream after the crystal removal which is not a blank stream. Appropriately in accordance with the invention, this next feed point is separated from the start of the filter by at least one fifth, preferably by at least one quarter, and more preferably by at least one third, of the length of the concentration zone (viewed from the buildup front).

When the position of the buildup front then shifts within the wash column owing to a perturbation, the value of $\Delta P_{SK}$ changes (provided that the position of the two measurement points within the wash column is retained). When the buildup front in FIG. 2 starts to move downward, $\Delta P_{SK}$ becomes smaller. This is the signal to reduce the control liquor flow rate and/or increase the suspension stream (4). When the buildup front in FIG. 2 starts to move upward, $\Delta P_{SK}$ becomes greater. This is the signal to increase the control liquor flow rate and/or reduce the suspension stream (4).

Experimentally, $\Delta P_{SK}$ can be derived in a simple manner by providing two open drillholes (positioned on the circumference of the wash column preferably one on top of the other, i.e. identically) in the cylindrical shell. One of the two drillholes is disposed at one height of the suspension zone (for example (8) in FIG. 2) and the other of the two drillholes is disposed, for example, at a height in the concentration zone (for example (7) in FIG. 2) or generally at a height within the zone projecting from the buildup front up to the end of the crystal bed. Lines attaching to the open drillholes lead in each case to the measurement head which directly determines the pressure difference existing between the two drill points and generally converts it to another signal, for example to an electrical signal.

When the two lines on the measurement head are conducted to one and the same height, the pressure difference detected in the measurement head normally no longer comprises the hydrostatic pressure difference existing between the two drillholes, i.e. it is automatically adjusted by the latter as a result of the measurement process employed. In this case, the measurement directly affords $\Delta P_{SKB}$. It will be appreciated that every line can also be conducted to a separate measurement head assigned to it. When the measurement heads are disposed at the same height, the relevant $\Delta P_{SKB}$ results by simple difference formation of the pressures detected in the measurement heads. In a particularly simple manner, $\Delta P_{SKB}$ can be determined with the aid of a pressure difference measurement membrane. One of the two lines ends on the left-hand side of the membrane and the other of the two lines ends on the right-hand side of the membrane. The measurement head comprising the membrane directly indicates $\Delta P_{SKB}$.

The two lines are preferably filled with liquid so that they do not block. Useful such liquids are, for example, mother liquor and pure melt. In the case of a suspension of water-soluble crystals (for example of acrylic acid crystals), it is also appropriate to use water as such a filling liquid. Firstly, water, unlike acrylic acid, does not have any tendency to free-radically polymerize and water also has marked dissolution capability for acrylic acid crystals growing in the open drillholes. The water preferably comprises a small amount of dissolved polymerization inhibitor (for example phenothiazione, monomethyl ether of hydroquinone, p-nitrosophenol, hydroquinone, nitrosodiethyl-aniline, 4-hydroxy-2,2,6,6-tetramethylpiperidine N-oxide and/or 4-oxo-2,2,6,6-tetra-methylpiperidine N-oxide). Appropriately, the aqueous filling of the lines is exchanged from time to time or continuously during the continuous operation of the wash column. Advantageously, the particular drillhole concludes smoothly on the inner side of the shell of the hydraulic wash column in order to form no resistance to the transport of the crystal bed.

The diameter of the entry orifice of such open drillholes is, viewed from the column interior, for the purpose of measuring $\Delta P_{SK}$, appropriately from an application point of view $\leq 5$ mm, often $\leq 3$ mm and in general $\geq 0.1$ mm. Appropriately from an application point of view, a drillhole diameter narrowing continuously or stepwise through the wall toward the column interior may be employed.

Preferably in accordance with the invention, an open drillhole along the concentration zone, based on the total length thereof, is disposed at least one third of the length, more preferably at least two thirds of the length and most preferably at least three quarters of the length, beyond the buildup front. It will be appreciated that the open drillhole along the concentration zone may also be disposed at filter height. Positioning of the $\Delta P_{SK}$ reference point not disposed in the suspension zone within the wash zone is less preferred in accordance with the invention.

Of course, the hydrostatic pressure difference can also be determined by calculation (the mass densities are known) and subtracted from the measured pressure difference $\Delta P_{SK}$ (for example when the lines are conducted from the open drillholes to pressure measurement heads disposed at different heights).

It will be appreciated that a plurality of open drillholes may also be provided at one and the same height along the concentration zone (or generally along the zone projecting from the buildup front up to the end of the crystal bed), distributed around the circumference of the hydraulic wash column (preferably uniformly). In this way, a plurality of pressure differences $\Delta P_{SK}$ can be determined simultaneously and utilized for determination (regulation) of the control liquor flow rate and/or of the suspension stream (4).

Advantageously in accordance with the invention, the flow rate of control liquor conducted or pumped back into the wash column and/or the flow rate of the suspension stream (4) conducted into the wash column are determined by using the ratio V of two pressure differences $(\Delta P_{SK})^1$ and $(\Delta P_{SK})^2$ (which have preferably both been adjusted by the particular accompanying hydrostatic pressure difference) whose particular reference points in the concentration zone (or generally in the zone projecting from the buildup front up to the end of the crystal bed) are at different heights. Their particular reference points in the suspension zone are preferably disposed at the same height. However, these may in principle also assume different height positions. It is also possible for one and the same reference point in the suspension zone to be used for both pressure differences.

In the steady operating state, this ratio V will have a value of >0 (the value 0 corresponds to a vanishing crystal bed length) and <1 (the value 1 corresponds to an unlimited crystal bed length), frequently $\geq 0.1$ (or $\geq 0.2$) and $\leq 0.8$. This is especially true when the two reference points not lying within the suspension zone lie within the concentration zone.

When the position of the buildup front changes, the value of V changes and induces a change in the flow rate of the control liquor and/or suspension (4). When the buildup front in FIG. 1 migrates upward, V grows and induces an increase in the flow rate of control liquor fed and/or a decrease in the flow rate of the suspension (4) fed. When the buildup front in FIG. 1 migrates downward, V falls and induces a decrease in the flow rate of control liquor fed and/or an increase in the flow rate of the suspension (4) fed.

The advantage of use of V as an indicator for a change in position of the buildup front is that causes other than a change in the position of the buildup front (for example a changed amount of liquid flowing through the crystal bed and/or changed crystal shapes and/or sizes) for a change in $\Delta P_{SK}$ have the same effect on $(\Delta P_{SK})^1$ and $(\Delta P_{SK})^2$ and therefore neutralize each other in the effect they have on the formation of the quotient V.

It is possible to experimentally derive $(\Delta P_{SK})^1$ and $(\Delta P_{SK})^2$ in a simple manner, for example by providing a further open drillhole (9) above the open drillhole (7) in a hydraulic wash column according to FIG. 2 along the concentration zone (or generally in the zone projecting from the buildup front up to the end of the crystal bed) (the open drillholes (7), (9) and (8) are preferably not offset from one another on the circumference of the hydraulic wash column, but rather provided one directly below another).

From the open drillhole (8), for example, a branching pressure line then leads by in each case one or the two branches to the left-hand side of a pressure measurement membrane in each case. On the right-hand side of one pressure measurement membrane, for example, the pressure line then leads from the open drillhole (9), and, on the right-hand side of the other pressure measurement membrane, the pressure line leads in a corresponding manner from the open drillhole (7).

It will be appreciated that a plurality of, for example up to 5 or 4, triples (preferably drilled at identical heights) of open drillholes (7), (8) and (9) may be provided around the circumference of the hydraulic wash column. In this way, a whole set of ratios V is simultaneously obtainable. Appropriately from an application point of view, the flow rates of control liquor and/or suspension (4) will be increased or reduced only when the majority of the ratios V has a deviation resolvable by the measurement technology in the same direction.

The driving pressure (reported as elevated pressure relative to atmospheric) in a hydraulic wash column is frequently up to 10 bar, in many cases up to 6 bar and often from 1 to 5 bar or from 0.5 to 4 bar. The hydraulic flow pressure drop of the mother liquor is generally from $\geq 100$ mbar to $\leq 5$ bar or $\leq 10$ bar.

The rotational speed of the blade is usually at values of >0 and $\leq 100$/min, or $\leq 60$/min. The temperature in the melt circuit is typically from 0.01 to 5° C., frequently from 0.1 to 3° C., above the melting point of the washed crystals removed.

The total height of the crystal bed in a hydraulic wash column is typically from 300 to 2000 mm, frequently from 500 to 1500 mm, in many cases from 400 mm to 1000 mm. The length of the filter elements is frequently from 20 to 200 mm. Regarding the filter perforation, the remarks on page 7 of WO 03/041833 can be followed. The length of the filter tube displacer is frequently from 100 to 500 mm. Typical internal diameters of a hydraulic wash column are from 300 to 3000 mm. Typical internal diameters of the filter tubes are from 5 to 200 mm, frequently from 10 to 100 mm, in many cases from 20 to 80 mm.

The number of filter tubes in the case of industrial scale application may, in accordance with the invention, be from 3 to 200 or more. The length of the wash zone is typically from 0.5 to 20 times, preferably from 1 to 8 times and more preferably from 2 to 5 times, the distance of the filter tube closest to the shell from the shell (this distance is generally from 25 to 500 mm, frequently from 40 to 250 mm, often from 80 to 200 mm).

According to the invention, it is advantageous when, in the ratio V of two (preferably adjusted) pressure differences $(\Delta P_{SK})^1$ and $(\Delta P_{SK})^2$, the distance between the two reference points which are preferably disposed in the concentration zone (or generally within the zone projecting from the buildup front up to the end of the crystal bed) (the distance between the corresponding open drillholes) is from 10 to 1000 mm, preferably from 50 to 500 mm and more preferably from 100 to 300 mm or 200 mm. The distance of the two reference points which are preferably disposed within the concentration zone and are closest to the buildup front from the buildup front is, appropriately in accordance with the invention, from 100 to 2000 mm, advantageously from 200 to 1000 mm.

The preferences for the inventive procedure lie in particular in its economic viability and in the fact that it is a continuously employable regulation and control process. It can be employed especially in hydraulic wash columns, as described in WO 03/041833 and in WO 03/041832. The differential temperature between mother liquor and pure melt may be up to 15° C. and more. In many cases, the differential temperature is from 4 to 10° C. and, in the case of low impurity content of the mother liquor, often even only from 2 to 4° C.

The process according to the invention is suitable, as already mentioned, especially for the purifying removal of acrylic acid crystals (or methacrylic acid crystals) from their suspension in contaminated acrylic acid melts (or methacrylic acid melts), as described in WO 01/77056, WO 02/055469 and WO 03/078378. This is true in particular when the acrylic acid crystals have a cubic to cuboidal appearance, and exhibit a length (L) to thickness (D) ratio in the range from L:D=1:1 to L:D=6:1, preferably in the range from 1:1 to 4:1 and more preferably in the range from 1.5:1 to 3.5:1. The thickness D of the crystals is typically in the range from 20 to 600 μm, often from 50 to 300 μm. The length L of the crystals is typically in the range from 50 to 1500 μm, often from 200 to 800 μm.

These are in particular suspensions which are obtainable, for example, by suspension crystallization of crude acrylic acids which comprise: from 65, or 70, or 75, or 85 to 99.5% by weight of acrylic acid, $\geq 0$, generally from 0.1 to 40% by weight, or up to 20% by weight of water,
$\geq 0$, generally from 0.001 to 5% by weight, of acrolein,
$\geq 0$, generally from 0.001 to 10% by weight, of methacrolein,
$\geq 0$, generally from 0.001 to 10% by weight, of methacrylic acid,
$\geq 0$, generally from 0.01 to 5% by weight, of acetic acid,
$\geq 0$, generally from 0.01 to 5% by weight, of propionic acid,
$\geq 0$, generally from 0.001 to 5% by weight, of formaldehyde,
$\geq 0$, generally from 0.001 to 5% by weight, of further aldehydes (under some certain circumstances also for each aldehyde, for example benzaldehyde), and
$\geq 0$, generally from 0.01 to 5% by weight, of maleic acid.

In particular, they are suspensions which are obtainable, for example, by suspension crystallization of crude acrylic acids which comprise:
$\geq 70\%$ by weight of acrylic acid,
up to 20% by weight of water,
up to 15% by weight of acetic acid,
up to 5% by weight of propionic acid,
up to 5% by weight of low molecular weight aldehydes,
up to 3% by weight of polymerization inhibitors and
up to 5% by weight of acrylic acid oligomers (Michael adducts).

In particular, they are suspensions which are obtainable, for example, by suspension crystallization of crude acrylic acids which comprise:
90 to 98% by weight of acrylic acid,
from 0.2 to 5% by weight of water,
from 0.001 to 3% by weight of acrolein,
from 0.001 to 3% by weight of methacrolein,
from 0.01 to 3% by weight of acetic acid,
from 0.001 to 3% by weight of propionic acid,
from 0.001 to 3% by weight of further aldehydes, and
from 0.001 to 3% by weight of maleic acid.

It is advantageous to carry out the suspension crystallization in at least two, or in at least three, suspension crystallizers operated in parallel. From these crystallizers, the crystal suspensions are conducted into a combined buffer vessel in which the resulting overall crystal suspension is continuously homogenized, mixed. From the buffer vessel, advantageously at least two, particularly advantageously at least three, hydraulic wash columns operated in parallel are fed. Both the startup of the suspension crystallizers operated in parallel and the startup of the hydraulic wash columns operated in parallel may be effected offset in time relative to one another or in parallel. In that case, encrustations are likewise formed offset in time and can correspondingly be removed offset in time.

The individual wash column and the individual suspension crystallizer are planned in engineering terms in such a way that two in operation can also take over the volumes of the third which may have failed.

Suspension crystallizers to be used with preference are described, for example, in WO 04/35514.

However, the process according to the invention is also suitable in the case of other crystal suspensions, as are described, for example, in EP-A 97405 with xylene crystal suspensions. It is also favorable in the case of N-vinylpyrrolidone crystal suspensions.

A significant advantage of the inventive procedure is that it can also be employed in the case of hydraulic wash columns which have a metallic shell. These may either be pure metals or alloys, for example carbon steels, iron-based alloys (stainless steel, for example with Cr/Ni addition) or nickel-based alloys (for example Hastelloy qualities). When the substance to be removed in a purifying manner is acrylic acid, the wall material is preferably stainless steel, especially stainless steel 1.4571, or 1.4541, or 1.4306, or 1.4404. The thickness of the metal wall delimiting the process chamber is appropriately from 3 to 30 mm, frequently from 4 to 20 mm and usually from 5 to 15 mm. The latter is especially true in the case of stainless steel.

The process according to the invention can also be employed when the shell of the hydraulic wash column is manufactured from glass or from synthetic plastic.

Typical values $\Delta P_{SK}$ or $\Delta P_{SKB}$ in the process according to the invention are frequently from 50 to 8000 mbar, in many cases from 100 to 4000 mbar, often from 200 to 1000 mbar, or up to 750 mbar.

Typical values V in the process according to the invention are from 0.1 to 0.8, frequently from 0.2 to 0.4.

In the process according to the invention, it is possible to regulate at the aforementioned values.

It will be appreciated that the regulation process according to the invention can be employed combined with the regulation processes disclosed in DE-A 10036881 and WO 02/09839.

A useful alternative process for this type is also a radiometric method for determining the flow rates of control liquor and/or suspension (4). In this process, a γ-radiator is used, which radiates into the crystal bed. The absorbance of the radiation as it passes through the crystal bed is dependent upon the length of the crystal bed and thus upon the position of the buildup front. This allows the flow rates of control liquor and/or suspension (4) also to be regulated (determined) in a very simple manner according to the weakening of the radiation signal.

In accordance with the present invention, it is preferable to select a substantially steady-state suspension stream (4) and to regulate the position of the buildup front substantially exclusively via the amount of the flow rate of the control liquor. In other words, the process of the present invention comprises in particular processes for controlling a hydraulic wash column which has a cylindrical shell (1) which delimits the column and within which one or more filter tubes (2) extend through the column parallel to the cylinder axis and have, in the vicinity of the second end of the column, at least one filter (3) in the filter tube wall which forms the sole direct connection between the filter tube interior under the pressure P1 and the interior of the column, in which at least one stream of a suspension (4) which comprises crystals of a substance to be purified suspended in a mother liquor is fed continuously into the first end of the column (5) with a pressure P2 (for example by means of a pump (6)) which is greater than P1, mother liquor (7) is conducted through the filters into the filter tube interior and out of the column via the filter tubes, control liquor (9) is fed into the wash column at the first end of the column and/or between this end and the start of the filter, the mother liquor and control liquor flow in the column form a crystal bed (10) of the substance to be purified, said crystal bed having a buildup front (11) which faces the first end of the column and at which crystals of the introduced suspension add continuously to the crystal bed, the crystal bed, by virtue of the force resulting from the hydraulic flow pressure drop of the mother liquor and control liquor flow in the column, is transported (13) past the filters into the wash zone disposed between the filters and the second end of the wash column (12), crystals are removed (14) continuously at the opposite end of the crystal bed to the buildup front, the removed crystals are melted (15) and a portion of the melt is passed (16) through the crystal bed as a wash liquid stream coming from the second end of the column against the transport direction of the crystals and the position of the buildup front is controlled with the aid of the flow rate of control liquor conducted into the wash column, wherein the flow rates of the control liquor conducted into the wash column are determined (regulated) by utilizing at least one pressure difference $\Delta P_{SK}$ which exists in the column between at least one point in the suspension zone (17) disposed in front of the buildup front and at least one point in the zone projecting from the buildup front up to the end of the crystal bed (preferably in the concentration zone (18), projecting up to the start of the wash zone (19), of the crystal bed).

EXAMPLE

By fractional condensation of a product gas mixture of a two-stage heterogeneously catalyzed gas phase partial oxidation of propene, in the side draw of a fractional condensation column, 1.5 t per hour of crude acrylic acid of the following composition contents were drawn off:

| | |
|---|---|
| acrylic acid | 96.1% by weight |
| acrolein | 446 ppm by weight |
| allyl acrylate | 20 ppm by weight |
| diacrylic acid | 3764 ppm by weight |
| acetic acid | 7460 ppm by weight |
| furfural | 6719 ppm by weight |
| benzaldehyde | 7131 ppm by weight |
| propionic acid | 751 ppm by weight |
| phenothiazine | 91 ppm by weight |
| MEHQ | 247 ppm by weight |
| water | 0.83% by weight. |

By continuous addition of 22.5 kg/h of water to the crude acrylic acid, its water content was increased to 2.3% by weight and it was subsequently fed to a suspension crystallizer at a temperature of 20° C. The crystallizer used was a cooling-disk crystallizer (manufacturer: GMF, Netherlands) with 7 cooling disks having a diameter of 1.25 m and a capacity of about 2500 l. As a coolant, a water/glycol mixture (70/30% by volume) was conducted through the cooling disks (inlet temperature=1.5 to 2° C). Melt and coolant were conducted in countercurrent. As it passed through the crystallizer, the melt was cooled to 8° C., which formed, based on the total mass of suspension, about 24% by weight of crystals.

A portion of this suspension was conducted continuously by means of a rotary piston pump (rotational speed-regulated) to a hydraulic wash column. This wash column had a cylindrical process chamber having internal diameter 263 mm and had a metal wall which delimited the process chamber and was made of 1.4571 stainless steel with wall thickness 5 mm. For liquid removal, a centrally installed filter tube (made of the same stainless steel) having an external diameter of 48 mm (wall thickness =2 mm) was used in the wash column. The length of the process chamber was 1230 mm.

The length of the filter tube was 1225 mm. The filter length was 60 mm. The filter was installed after a pipe length of 970 mm (measured from the top). The crystals were removed at the lower end of the wash column with a rotating blade (60 revolutions per minute). The transport direction was from the top downward.

Figure 3:
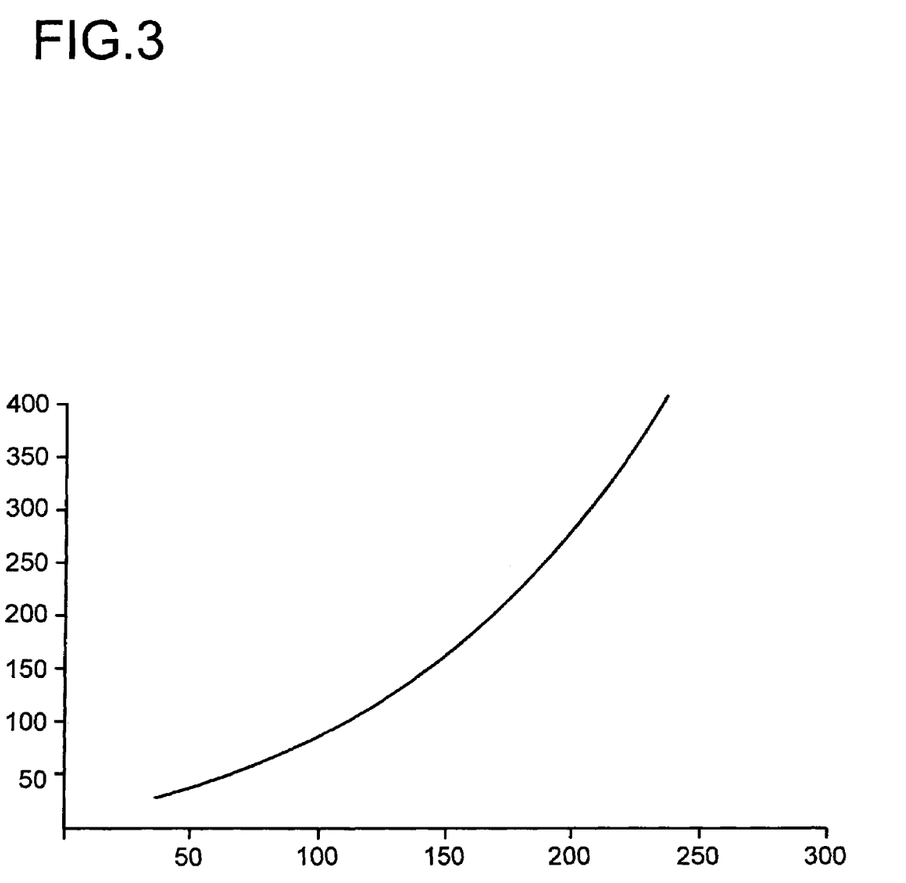
FIG. 3 is a typical profile $\Delta P_{SKB}$ (ordinate, mbar) as a function of the distance (abscissa, mm) between buildup front and second open drillhole with the same position of the first open drillhole.

The removed crystals were resuspended in a melt circuit which was operated at 14° C. (melting point of the crystals removed in a purifying manner). At the same time, MEHQ (monomethyl ether of hydroquinone) and air (by sparging) were introduced as polymerization inhibitors into the circulated suspension (278 ppm by weight of MEHQ). Heat was introduced into the circulated suspension by an indirect route via a heat exchanger, in order to substantially melt the crystals resuspended therein. The pump used in the melt circuit was a centrifugal pump (1500 rpm) with double-action axial face seal. The barrier fluid used was a water/glycol mixture (85/15% by volume) which was cooled indirectly with cooling water. The position of the wash front in the column was monitored by a plurality of the thermometers installed axially at different heights in the wash column, and regulated with adjustment of the amount of pure product drawn off from the melt circuit. The crystal bed height (the buildup front) was controlled with regulation to the adjusted pressure difference $\Delta P_{SKB}$=250 mbar which existed between a first open drillhole within the suspension zone and a second open drillhole 300 mm below the first open drillhole in the steady state (FIG. 3 shows a typical profile $\Delta P_{SKB}$ (ordinate, mbar) as a function of the distance (abscissa, mm) between buildup front and second open drillhole with the same position of the first open drillhole). The hydraulic wash column was charged with a suspension flow rate of 1400 kg/h from the cooling-disk crystallizer. The temperature of the suspension was 8° C. An elevated pressure relative to atmospheric of from 2.0 to 2.2 bar was established at the top of the wash column, which varied in a narrow range about the average of 2.05 bar. The elevated pressure at the lower end of the column was from 1.8 to 2.0 bar. The control stream (a divisional stream of the stream flowing off through the filter) returned to the wash column (into the feed of the suspension downstream of the rotary piston pump) by means of a control stream pump in the steady state was 1400 kg/h.

The pure product stream of purified acrylic acid drawn off from the melt circuit was 325 kg/h. This corresponds to a yield of 96.7% by weight based on the crystal mass stream fed to the wash column with the suspension. The pure product had the following composition contents:

| | |
|---|---|
| acrylic acid | 99.75% by weight, |
| acrolein | not detectable, |
| allyl acrylate | not detectable, |
| acetic acid | 1457 ppm by weight, |
| furfural | 3 ppm by weight, |
| benzaldehyde | 2 ppm by weight, |
| propionic acid | 209 ppm by weight, |
| phenothiazine | not detectable, |
| MEHQ | 278 ppm by weight, |
| water | <0.05% by weight. |

Wash front and buildup front were of satisfactory stability over the entire experiment.

US Provisional Patent Application No. 60/673339, filed on Apr. 21, 2005, is incorporated into the present application by literature reference. With regard to the abovementioned teachings, numerous alterations and deviations from the present invention are possible. It is therefore possible to assume that the invention, within the scope of the appended claims, can be performed in a different way from that specifically described herein.

What is claimed is:

1. A process for controlling a hydraulic wash column which has a cylindrical shell (1) which delimits the column and within which one or more filter tubes (2) extend through the column parallel to the cylinder axis and have, in the vicinity of the second end of the column, at least one filter (3) in the filter tube wall which forms the sole direct connection between the filter tube interior under the pressure P1 and the interior of the column, in which at least one stream of a suspension (4) which comprises crystals of a substance to be purified suspended in a mother liquor is fed continuously into the first end of the column (5) with a pressure P2 which is greater than P1, mother liquor (7) is conducted through the filters into the filter tube interior and out of the column via the filter tubes, optionally control liquor (9) is fed into the wash column at the first end of the column and/or between this end and the start of the filter, the mother liquor and, optionally control liquor flow in the column form a crystal bed (10) of the substance to be purified, said crystal bed having a buildup front (11) which faces the first end of the column and at which crystals of the introduced suspension add continuously to the crystal bed, the crystal bed, by virtue of the force resulting from the hydraulic flow pressure drop of the mother liquor and, optionally control liquor flow in the column, is transported (13) past the filters into the wash zone disposed between the filters and the second end of the wash column (12), crystals are removed (14) continuously at the opposite end of the crystal bed to the buildup front, the removed crystals are melted (15) and a portion of the melt is passed (16) through the crystal bed as a wash liquid stream coming from the second end of the column against the transport direction of the crystals and the position of the buildup front is controlled with the aid of the flow rate of control liquor conducted into the wash column and/or with the aid of the flow rate of the suspension (4) conducted into the wash column, wherein the flow rates of the control liquor and/or suspension (4) conducted into the wash column are determined by utilizing at least one pressure difference $\Delta P_{SK}$ which exists in the column between at least one point in the suspension zone (17) disposed in front of the buildup front and at least one point in the zone projecting from the buildup front up to the end of the crystal bed.

2. The process according to claim 1, wherein the flow rates of control liquor and/or suspension (4) fed into the wash column are determined by using the ratio V of two pressure differences $(\Delta P_{SK})^1$ and $(\Delta P_{SK})^2$ whose particular reference points are disposed at different heights in the zone projecting from the buildup front up to the end of the crystal bed.

3. The process according to claim 1, wherein $\Delta P_{SK}$ is from 50 to 8000 mbar.

4. The process according to claim 2, wherein V is from 0.1 to 0.8.

5. The process according to either of claims 2 and 4, wherein the distance of the two reference points within the zone projecting from the buildup front up to the end of the crystal bed is from 10 to 1000 mm.

6. The process according to any of claims 1 to 5, wherein the particular pressure difference $\Delta P_{SK}$ used is used in its form $\Delta P_{SKB}$ adjusted by the particular accompanying hydrostatic pressure difference.

7. The process according to any of claims 1 to 6, wherein the crystals suspended in the suspension stream are acrylic acid crystals.

8. The process according to claim 1, wherein the flow rates of the control liquor and/or suspension (4) conducted into the wash column are determined by utilizing at least one pressure difference $\Delta P_{SK}$ which exists in the column between at least one point in the suspension zone (17) disposed in front of the buildup front and at least one point in the zone projecting from the buildup front up to the end of the crystal bed which is in the concentration zone (18), projecting up to the start of the wash zone (19), of the crystal bed.

* * * * *